United States Patent
Yin et al.

(10) Patent No.: US 10,059,753 B2
(45) Date of Patent: Aug. 28, 2018

(54) MUTANT CHICKEN INTERLEUKIN-1β PROTEIN AS CHICKEN INTERLEUKIN-1β ANTAGONIST AND USES THEREOF

(71) Applicant: National Tsing Hua University, Hsinchu (TW)

(72) Inventors: Hsien-Sheng Yin, Hsinchu (TW); Wen-Ting Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/260,017

(22) Filed: Sep. 8, 2016

(65) Prior Publication Data

US 2018/0009867 A1   Jan. 11, 2018

(30) Foreign Application Priority Data

Jul. 6, 2016   (TW) .............................. 105121405 A

(51) Int. Cl.
*C07K 14/545*   (2006.01)
*A61K 38/00*   (2006.01)

(52) U.S. Cl.
CPC ............ *C07K 14/545* (2013.01); *A61K 38/00* (2013.01)

(58) Field of Classification Search
None
See application file for complete search history.

(56) References Cited

PUBLICATIONS

Chen, Wen-Ting et al., "Structure and function of chicken interleukin-1 beta mutants: uncoupling of receptor binding and in vivo biological activity", Scientific Reports, Jun. 9, 2016, 6:27729, pp. 1-11.

*Primary Examiner* — Dong Jiang
(74) *Attorney, Agent, or Firm* — WPAT, PC

(57) ABSTRACT

The present invention provides a mutant chicken interleukin-1β protein as a chicken interleukin-1β antagonist, which has a substituted peptide at position 117 and/or 118 of wild-type chicken interleukin-1β peptides. The mutant chicken interleukin-1β protein is created by using point mutation in a method genetic engineering; it can significantly inhibit proliferation of avian virus, such as avian influenza virus, avian reovirus and Marek's disease virus, and avian inflammation response. Therefore, the mutant chicken interleukin-1β protein of the present invention can be used as antiviral and anti-inflammatory medication.

6 Claims, 15 Drawing Sheets
Specification includes a Sequence Listing.

ARV

ARV+E118R

ମUTANT CHICKEN INTERLEUKIN-1β PROTEIN AS CHICKEN INTERLEUKIN-1β ANTAGONIST AND USES THEREOF

CROSS-REFERENCE TO RELATED APPLICATION

This application claims the priority of Taiwanese patent application No. 105121405, filed on Jul. 6, 2016, which is incorporated herewith by reference.

BACKGROUND OF THE INVENTION

1. Field of the Invention

The present invention relates to a mutant chicken interleukin-1β protein, and in particular, to a mutant chicken interleukin-1β protein as a chicken interleukin-1β antagonist.

2. The Prior Arts

The poultry industry in global continues to show impressive growth year by year. Therefore, the poultry farm in developed areas use a high density confinement rearing method to increase breeding density, which causes an urgent problem, government agency should spend more effort into biosecurity and disease prevention. In recent years, some countries have been faced the difficult challenges of a dramatic increase in the incidence of infectious disease outbreaks, some result from poor hygiene and management, but most of which result from a highly aggressive strain of virus, such as highly pathogenic avian influenza virus causing human infection, avian reovirus causing viral arthritis, lethal Newcastle disease virus and Marek's disease virus causing tumours in chicken flocks.

Recently, among five legally infectious diseases in Taiwan, the infectious disease caused by avian reovirus needs to detect antibody. Although a vaccine against avian reovirus is usually used, there is still a lot of chickens in the poultry farms affected by an avian reovirus condition, including arthritis, tenosynovitis, mal-absorption syndrome; ducks in Fujian coast are usually infected with avian reovirus to suffer from arthritis, which is called Muscovy duck reovirus, and the virus seriously affects the duck breeding rate resulting in huge economic loses in the poultry production industry. Therefore, the vaccine against legally infectious disease still fails to totally protect poultry from avian reovirus infection. In addition to vaccine, it needs other effective and rapid prevention measure to control an infectious-disease outbreak.

SUMMARY OF THE INVENTION

As such, the present invention provides a mutant chicken interleukin-1β protein, which is created by point mutation in a genetic engineering method. The mutant chicken interleukin-1β protein of the present invention can be a chicken interleukin-1β antagonist to inhibit avian inflammation response, to inhibit the replication and proliferation of avian virus, and to enhance the antiviral ability. Therefore, the mutant chicken interleukin-1β protein of the present invention can be used as anti-inflammatory medication for a novel therapy.

A primary objective of the present invention is to provide a mutant chicken interleukin-1β protein, which has a substitution mutation at a position 117 and/or 118 of SEQ ID NO: 1.

Another objective of the present invention is to provide a chicken interleukin-1β antagonist, which is the mutant chicken interleukin-1β protein.

A further objective of the present invention is to provide a method of treating a disease caused by avian virus infection, comprising administering to a subject an effective amount of a medicament including a chicken interleukin-1β antagonist.

According to an embodiment of the present invention, the chicken interleukin-1β antagonist is the mutant chicken interleukin-1β protein.

According to an embodiment of the present invention, the avian virus infection is avian reovirus, avian influenza virus, Marek's disease virus or Newcastle disease virus infection.

According to an embodiment of the present invention, the medicament is administered via an oral route or an intravenous injection.

According to an embodiment of the present invention, the mutant chicken interleukin-1β protein inhibits proliferation of avian virus and avian inflammation response.

According to an embodiment of the present invention, the substitution mutation is a T117A, E118K, E118R, E118A substitution mutation of SEQ ID NO: 1.

Accordingly, the mutant chicken interleukin-1β protein of the present invention has a potential to be a chicken interleukin-1β antagonist, which can effectively inhibit avian inflammation response and proliferation of avian reovirus, the mutant chicken interleukin-1β protein also are effective for both prevention and treatment against highly pathogenic avian influenza virus. The present invention is to get rid of the traditional characteristics of an antiviral drug that is effective against a single virus, it designs and creates an immune molecule focused on host's own immune system because some avian viruses, such as avian influenza virus, avian reovirus, Newcastle disease virus and Marek's disease virus, hijack immune cell to spread infection. Therefore, the mutant chicken interleukin-1β protein of the present invention can use in biological medicine, livestock and antiviral drugs production.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
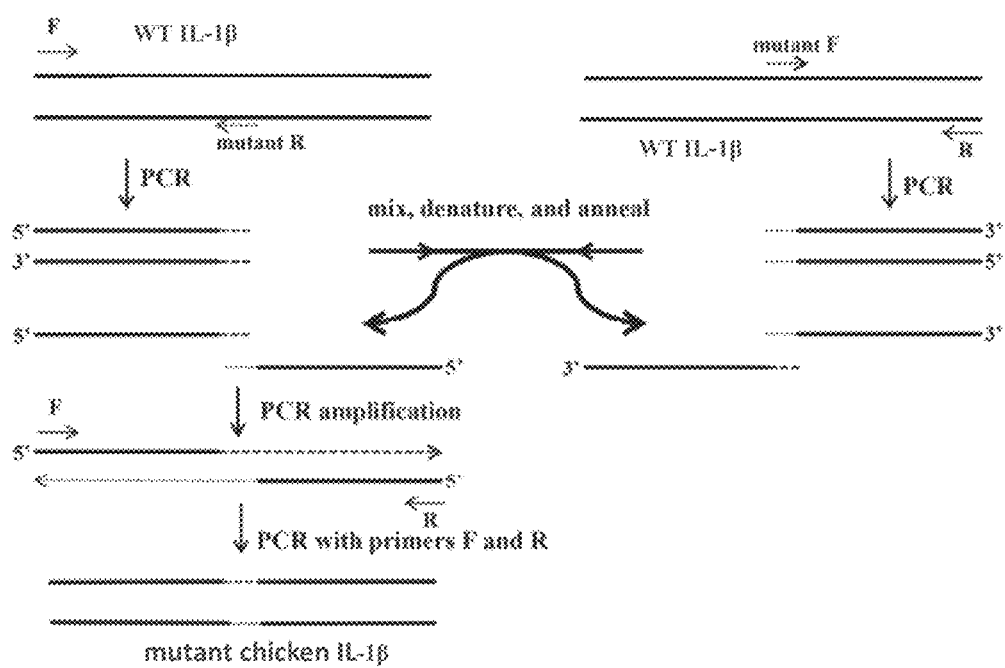
FIG. 1 is a flow chart of constructing the mutant chicken interleukin-1β (IL-1β) protein in one embodiment of the present invention.

The accompanying drawings are included to provide a further understanding of the invention, and are incorporated in and constitute a part of this specification. The drawings illustrate embodiments of the invention and, together with the description, serve to explain the principles of the invention.

The present invention uses the pro-inflammatory cytokines interleukin-1β(IL-1β) to be a target because it can cause a series of inflammatory response as a bridge between innate and acquired immune systems, and the immune cells are likely to be a proliferative target for avian influenza virus and avian reovirus. The present invention provides a mutant chicken interleukin-1β protein by point mutation in the key amino acids (at amino acid position 117 and 118) of wild-type chicken IL-1β in a genetic engineering method, obtains a soluble protein with high yield and high purity by high performance protein expression and purification platform, and validates the mutant chicken interleukin-1β protein having anti-inflammatory effect by immune response in an animal's system, In addition, the present invention validates that the secondary structure of the mutant chicken interleukin-1β protein has the same receptor binding affinity with wild-type chicken IL-1β, and it indeed is a wild-type chicken interleukin-1β antagonist by signaling pathway in vitro competitive test.

To validate the chicken interleukin-1β antagonist of the present invention can inhibit virus infection, injecting avian reovirus or avian reovirus mixing with the mutant chicken interleukin-1β protein of the present invention into specific pathogen free (SPF) chicken, respectively, and immunohistochemical staining using specific monoclonal antibody against avian reovirus. The result shows that viral proliferation in the tissue inoculated with virus mixing with the mutant chicken interleukin-1β protein of the present invention is significantly less than the tissue only inoculated with virus. Also, it has been reported that mRNA expression of IL-1β associated with inflammatory and immune response is increased after infection with avian influenza virus (Cellular and Molecular Immunology. 2008. 5(2):113-120), Marek's disease virus (Viral Immunology. 2008. 21(2):203-214) and Newcastle disease virus (Virology Journal 2016. 13:41), which is the same the mRNA expression of IL-1β after infection with avian reovirus. Therefore, the present invention is to get rid of the traditional characteristics of an antiviral drug that is effective against a single virus, it designs and creates an immune molecule focused on host's own immune system because some avian viruses hijack immune cell to spread infection.

Definition

Unless otherwise defined, all technical and scientific terms used herein have the same meaning as commonly understood by one of ordinary skill in the art to which this invention pertains. In the case of conflict, the present document, including definitions will control.

As used herein, "avian virus" refers to a virus infected bird, including but not limited to avian reovirus, avian influenza virus, Marek's disease virus and Newcastle disease virus.

As used herein, "T117A" refers to threonine at the position 117 substituted with alanine; "E118K" refers to glutamic acid at the position 118 substituted with lysine; "E118R" refers to glutamic acid at the position 118 substituted with arginine; and "E118A" refers to glutamic acid at the position 118 substituted with alanine.

Example 1

Construct the Mutant Chicken Interleukin-1β Protein

Referring to FIG. 1 shows the flow chart of constructing the mutant chicken interleukin-1β protein in one embodiment of the present invention. The present invention designs a wild-type (WT) chicken interleukin-1β sequence (SEQ ID NO:1) to have a point mutation, which is obtained from predicting an amino acid position that may affect biological activity by using a 3D structure of WT chicken interleukin-1β and its receptors, the point mutations are T117A, E118K or E118R, respectively. Therefore, the present mutation constructs the mutant chicken interleukin-1β sequence having T117A (SEQ ID NO:2) and the mutant chicken interleukin-1β sequence having E118K (SEQ ID NO:3) and the mutant chicken interleukin-1β sequence having E118R (SEQ ID NO:4).

First, designing the forward and reverse primers comprising the point mutation for the three point mutation sequences of chicken interleukin-1β protein (SEQ ID NO:2, SEQ ID NO: 3 and SEQ ID NO: 4), wherein T117A forward and reverse primers of the T117A mutation sequence (SEQ ID NO:2) respectively are SEQ ID NO: 5 and SEQ ID NO: 6; E118K forward and reverse primers of E118K mutation sequence (SEQ ID NO:3) respectively are SEQ ID NO:7 and SEQ ID NO:8; E118R forward and reverse primers of E118R mutation sequence (SEQ ID NO:4) respectively are SEQ ID NO:9 and SEQ ID NO:10.

And, using polymerase chain reaction to amplify WT chicken interleukin-1β sequence (SEQ ID NO:1) for the mutation, wherein WT chicken interleukin-1β sequence is as a template (SEQ ID NO:1), the forward primer of WT chicken interleukin-1β (SEQ ID NO:11) and T117A reverse primer (SEQ ID NO: 6) amplify T117A mutation to obtain the first fragment of T117A mutation sequence (SEQ ID NO: 13), T117A forward primer (SEQ ID NO:5) and the reverse primer of WT chicken interleukin-1β (SEQ ID NO: 12) amplify T117A mutation to obtain the second fragment of T117A mutation sequence (SEQ ID NO: 14); wherein WT chicken interleukin-1β sequence is as a template (SEQ ID NO:1), the forward primer of WT chicken interleukin-1β (SEQ ID NO:11) and E118K reverse primer (SEQ ID NO: 8) amplify E118K mutation to obtain the first fragment of E118K mutation sequence (SEQ ID NO: 15), E118K forward primer (SEQ ID NO:7) and the reverse primer of WT chicken interleukin-1β (SEQ ID NO: 12) amplify E118K mutation to obtain the second fragment of E118K mutation sequence (SEQ ID NO: 16); and wherein WT chicken interleukin-1β sequence is as a template (SEQ ID NO:1), the forward primer of WT chicken interleukin-1β (SEQ ID NO:11) and E118R reverse primer (SEQ ID NO: 10) amplify E118R mutation to obtain the first fragment of E118R mutation sequence (SEQ ID NO: 17), E118R forward primer (SEQ ID NO:9) and the reverse primer of WT chicken interleukin-1β (SEQ ID NO: 12) amplify E118R mutation to obtain the second fragment of E118R mutation sequence (SEQ ID NO: 18).

Then, the first fragment (SEQ ID NO: 13) and second fragment (SEQ ID NO: 14) of T117A mutation sequence serve as templates and primers for extension to obtain the mutant chicken interleukin-1β sequence having T117A mutation (SEQ ID NO:2); the first fragment (SEQ ID NO: 15) and second fragment (SEQ ID NO: 16) of E118K mutation sequence serve as templates and primers for extension to obtain the mutant chicken interleukin-1β sequence having E118K mutation (SEQ ID NO:3); and the first fragment (SEQ ID NO: 17) and second fragment (SEQ ID NO: 18) of E118R mutation sequence serve as templates and primers for extension to obtain the mutant chicken interleukin-1β sequence having E118R mutation (SEQ ID NO:4).

Furthermore, amplifying the mutant chicken interleukin-1β sequence having T117A mutation (SEQ ID NO:2) as template using the forward (SEQ ID NO:11) and reverse (SEQ ID NO:12) primers of WT chicken interleukin-10; amplifying the mutant chicken interleukin-1β sequence having E118K mutation (SEQ ID NO:3) as template using the forward (SEQ ID NO:11) and reverse (SEQ ID NO:12) primers of WT chicken interleukin-10; and amplifying the mutant chicken interleukin-1β sequence having E118R mutation (SEQ ID NO:4) as template using the forward (SEQ ID NO:11) and reverse (SEQ ID NO:12) primers of WT chicken interleukin-1β.

Figure 2:
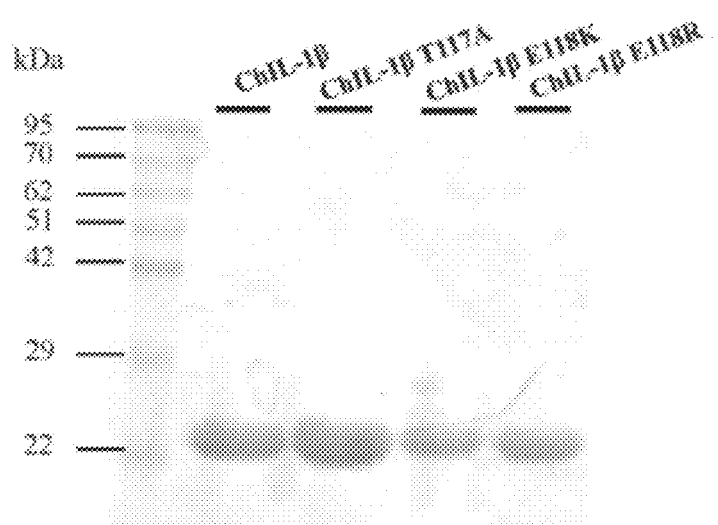
FIG. 2 is 12% sodium dodecyl sulfate polyacrylamide gel electrophoresis (SDS PAGE) of the mutant chicken interleukin-1β (IL-1β) protein of the present invention after clone, mutant protein expression and purification. ChIL-1β is indicated wild-type chicken interleukin-1β; ChIL-1β T117A is indicated the mutant chicken interleukin-1β protein having T117A mutation; ChIL-1β E118K is indicated the mutant chicken interleukin-1β protein having E118K mutation; and ChIL-1β E118R is indicated the mutant chicken interleukin-1β protein having E118R mutation.

Finally, cloning, expressing and purifying WT chicken interleukin-1β sequence (SEQ ID NO: 1), the mutant chicken interleukin-1β sequence having T117A mutation (SEQ ID NO: 2), the mutant chicken interleukin-1β sequence having E118K mutation (SEQ ID NO: 3), and the mutant chicken interleukin-1β sequence having E118R mutation (SEQ ID NO: 4). As shown in FIG. 2, the molecular weight of WT chicken IL-1β (ChIL-1β) and the mutant chicken interleukin-1β protein having T117A (ChIL-1β T117A), E118K (ChIL-1β E118K) and E118R (ChIL-1β E118R) mutation is 23.6 kDa by 12% sodium dodecyl sulfate polyacrylamide gel electrophoresis (SDS PAGE).

Example 2

Bioactivity Assay of the Mutant Chicken Interleukin-1β Protein

Figure 3:
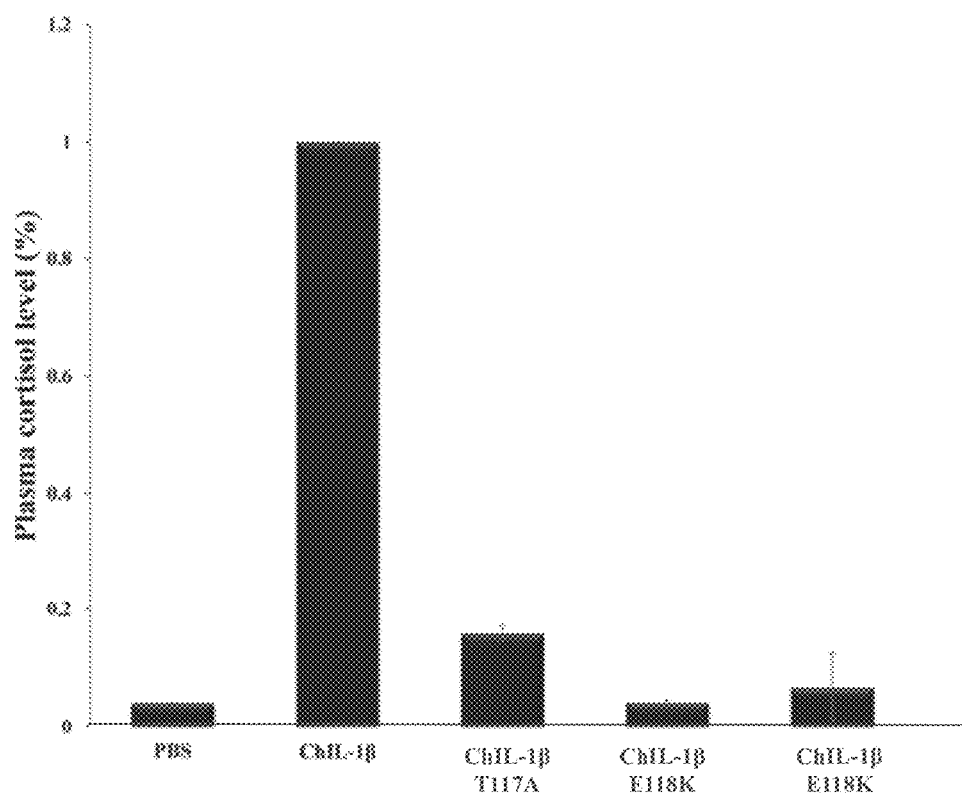
FIG. 3 shows that the plasma cortisol levels in chickens administrated the mutant chicken interleukin-1β protein. PBS is indicated phosphate-buffered saline; ChIL-1β is indicated wild-type chicken interleukin-1β; ChIL-1β T117A is indicated the mutant chicken interleukin-1β protein having T117A mutation; ChIL-1β E118K is indicated the mutant chicken interleukin-1β protein having E118K mutation; and ChIL-1β E118R is indicated the mutant chicken interleukin-1β protein having E118R mutation.

To determine the in vivo activity of the mutant chicken interleukin-1β, the present invention detects the plasma cortisol level after respectively injecting the mutant chicken interleukin-1β proteins having T117A, E118K or E118R mutation into the wing vein of specific pathogen free (SPF) chicken. As shown in FIG. 3, the plasma cortisol levels are significantly decreased in chickens administrated via intravenous injections of the mutant chicken interleukin-1β protein having T117A (ChIL-1β T117A), E118K (ChIL-1β E118K) or E118R (ChIL-1β E118R) mutation. The plasma cortisol level resulted from responses to the mutant chicken interleukin-1β protein having T117A, E118K or E118R mutation relative to that of WT chicken interleukin-1β protein are 16%, 4% and 10%, respectively. The mutant chicken interleukin-1β protein having E118K mutation does not induce an increased plasma cortisol level which is similar to the result of injecting phosphate-buffered saline (PBS). Therefore, the mutant chicken interleukin-1β protein of the present invention can block in vivo chicken pro-inflammatory immune responses.

Example 3

The Secondary Structures of the Mutant Chicken Interleukin-1β Protein

To determine if the mutant chicken interleukin-1β protein of the present invention wound substantially disrupt their tertiary structures and would thereby case reduction in biological activity, the present invention assesses the secondary structure of WT chicken IL-1β and the mutant chicken interleukin-1β protein having T117A, E118K or E118R mutation by far-UV CD spectroscopy.

Figure 4:
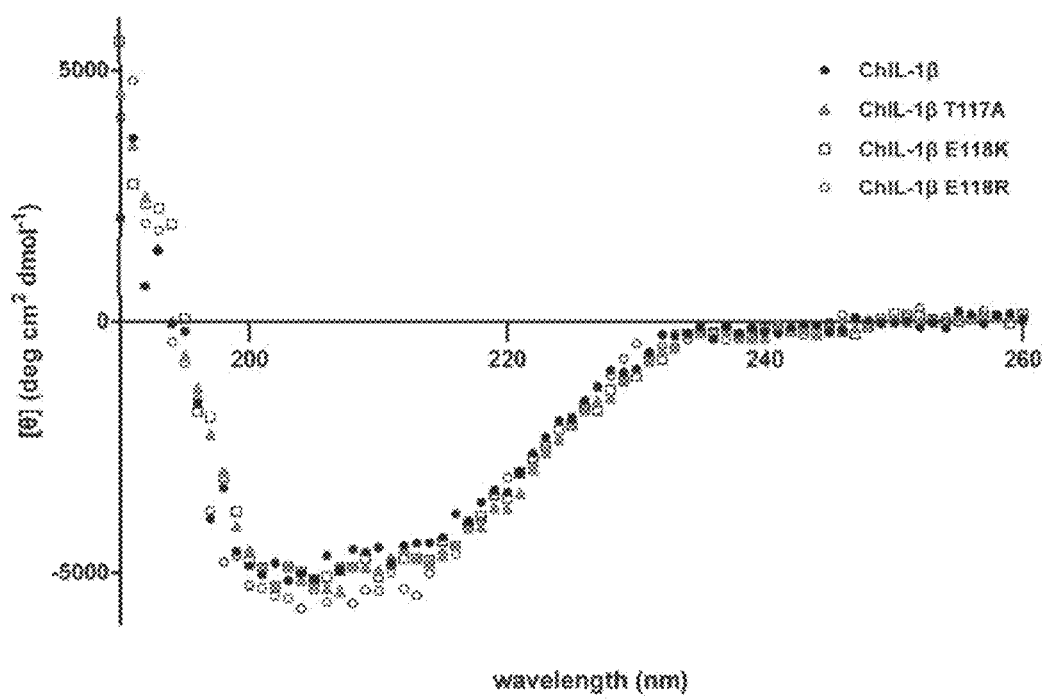
FIG. 4 shows the secondary structures of the mutant chicken interleukin-1β by far-UV CD spectroscopy. ChIL-1β is indicated wild-type chicken interleukin-1β; ChIL-1β T117A is indicated the mutant chicken interleukin-1β protein having T117A mutation; ChIL-1β E118K is indicated the mutant chicken interleukin-1β protein having E118K mutation; and ChIL-1β E118R is indicated the mutant chicken interleukin-1β protein having E118R mutation.

As shown in FIG. 4, the spectra of the four above-mentioned proteins are nearly identical and have minima at 206 nm, which indicates the presence of β-sheet. The result indicates that the mutant chicken interleukin-1β protein of the present invention cause reduction in biological activity which does not result from the secondary structure change.

Example 4

The Binding Affinity of the Mutant Chicken Interleukin-1β Protein

To assess if the significantly reduced biological activity of the mutant chicken interleukin-1β protein of the present invention is a consequence of reduced-receptor-binding activity, a surface plasmon resonance (SPR) study is performed using immobilized IL-1 receptor and WT chicken IL-1β, the mutant chicken interleukin-1β protein having T117A or E118K mutation.

Figure 5A:
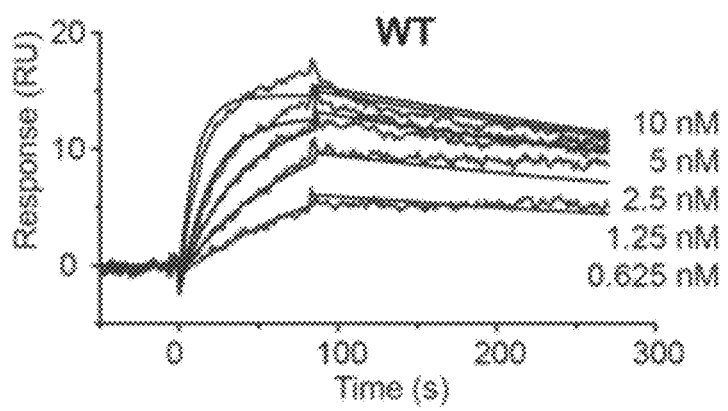
FIGS. 5A to 5C show the binding affinities of the mutant chicken interleukin-1β protein. WT is indicated wild-type chicken interleukin-1β; T117A is indicated the mutant chicken interleukin-1β protein having T117A mutation; and E118K is indicated the mutant chicken interleukin-1β protein having E118K mutation.
Figure 5B:
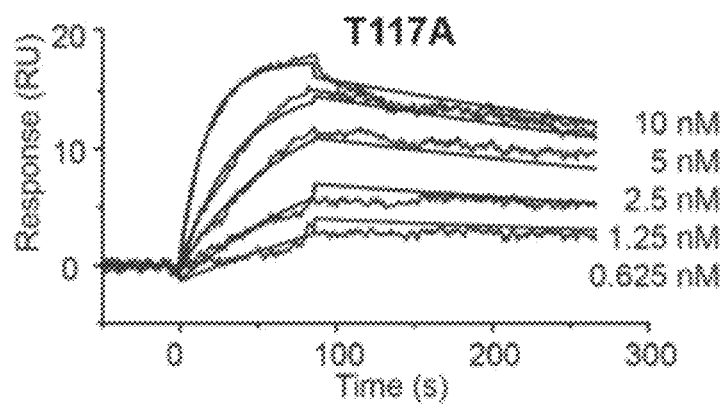
Figure 5C:
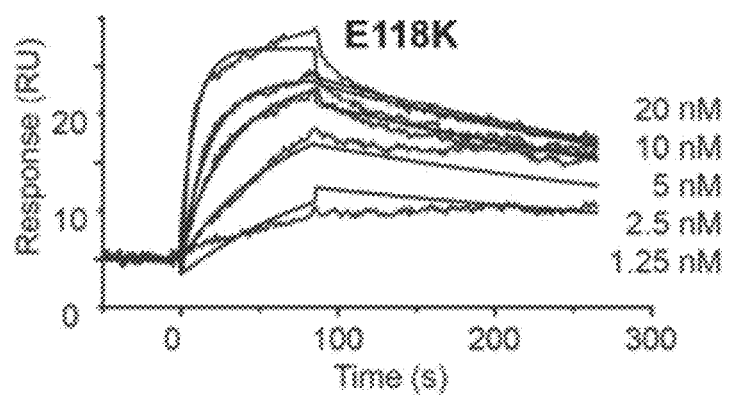

As shown in FIGS. 5A to 5C, the Kd values for WT chicken IL-1β protein, the mutant chicken interleukin-1β protein having T117A or E118K mutation are 0.12, 0.23 and 0.37 nM, respectively. The result suggests that these protein have similar receptor binding affinities compared with WT chicken IL-1β, they seem to have no great effect on receptor binding even though they significantly reduce biological activity, which indicates that the mutant chicken interleukin-1β protein may be involved in signal transduction once IL-1β has bound to the receptor.

Example 5

The Effects of the Mutant Chicken Interleukin-1β Protein on IL-1β Signal Transduction To evaluate the effects of the mutant chicken interleukin-1β protein on IL-1β signal transduction, IL-6 production induced by chicken IL-1β is evaluated by measuring the IL-6 expression level in chicken fibroblast cell lysates.

Figure 6A:
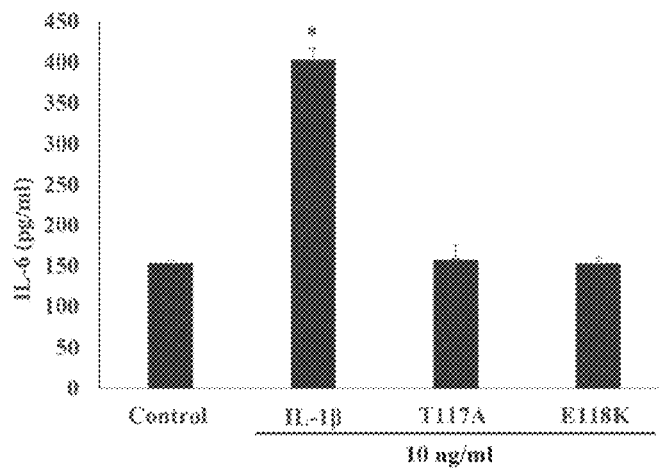
FIGS. 6A and 6B show the effect of the mutant chicken interleukin-1β protein on signal transduction. Control is indicated chicken fibroblast cell; IL-1β is indicated wild-type chicken interleukin-1β; T117A is indicated the mutant chicken interleukin-1β protein having T117A mutation; and E118K is indicated the mutant chicken interleukin-1β protein having E118K mutation.

As shown in FIG. 6A, the elevation of IL-6 expression induced by dose-dependent WT chicken IL-1β is highest, while the mutant chicken interleukin-1β protein having T117A or E118K mutation is an indistinguishable effect on IL-6 production from that of control, which indicates that only WT chicken IL-1β shows effect on signal transduction, but the mutant chicken interleukin-1β protein of the present invention show no effect on signal transduction.

Figure 6B:
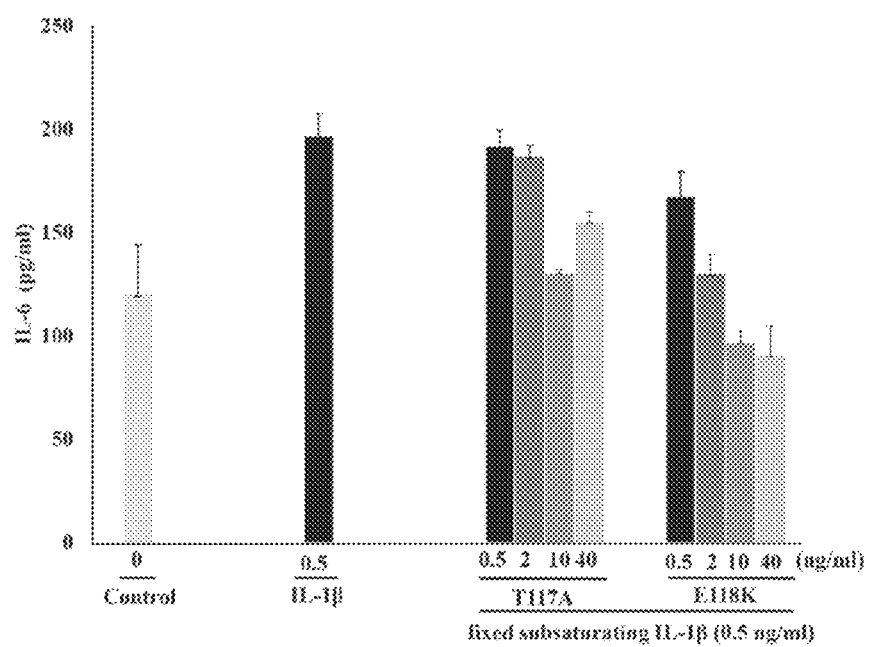

Therefore, the present invention further determines whether the mutant chicken interleukin-1β protein antagonizes chicken IL-1β activity, which is validated by competitive examination for cellular signaling. As shown in FIG. 6B, chicken fibroblast cells are treated with increasing concentration of the mutant chicken interleukin-1β protein in the presence of fixed subsaturating concentration of WT IL-1β. The mutant chicken interleukin-1β protein exhibits dose-dependent inhibition of IL-1β-induced IL-6 production to act as antagonists, as well as competes for IL-1β to block IL-1β signal transduction.

Example 6

3D Structure of the Mutant Chicken Interleukin-1β Protein

To examine the difference between crystal structure of the mutant chicken interleukin-1β protein and WT chicken IL-1β, the present invention uses X-ray crystallographic structure determination platform to detect the 3D structure of the mutant chicken interleukin-1β protein having T117A or E118K mutation.

Figure 7A:
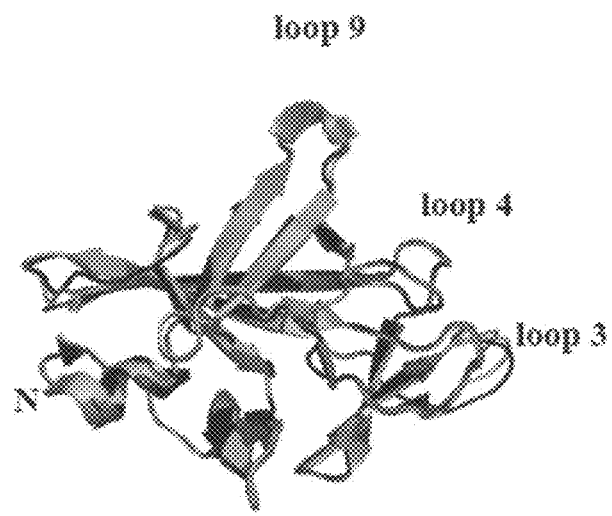
FIGS. 7A to 7D show the 3D structure of the mutant chicken interleukin-1β protein. A is the structural difference between wild-type chicken interleukin-1β and the mutant chicken interleukin-1β protein; B shows 3D structure of wild-type chicken interleukin-1β; C shows 3D structure of the mutant chicken interleukin-1β protein having T117A mutation; D shows 3D structure of the mutant chicken interleukin-1β protein having E118K mutation.
Figure 7B:
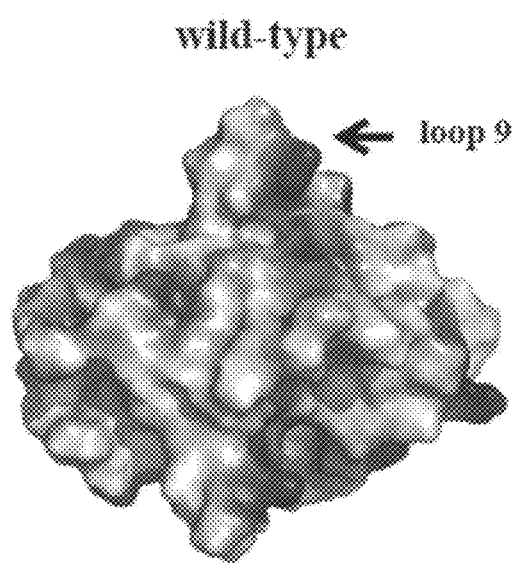
Figure 7C:
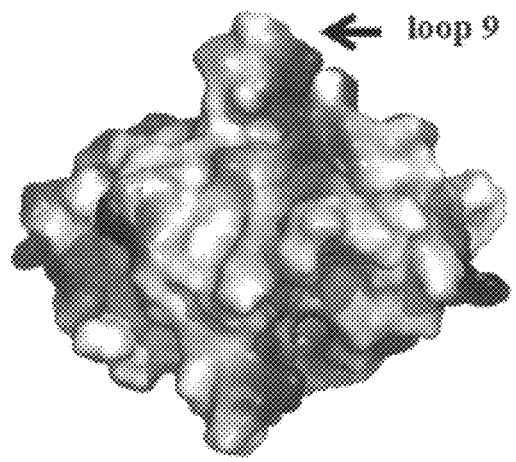
Figure 7D:
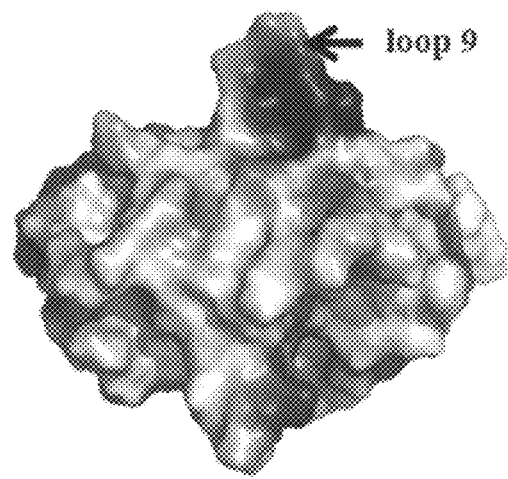

As shown in FIGS. 7A to 7D, the crystal structure of the mutant chicken interleukin-1β protein nearby amino acid change region is most different from WT chicken IL-1β. Close examination reveals that the 116-118 residues form a loop in WT chicken IL-1β (FIG. 7A black region), but a short α-helix in the mutant chicken interleukin-1β protein (FIG. 7A, gray and light gray region). The present invention uses crystal structure to generate electrostatic potential maps for WT chicken IL-1β and the mutant chicken interleukin-1β protein. The charge distributions near loop 9 differ for WT chicken IL-1β and the mutant chicken interleukin-1β protein. The loop 9 region is predominantly negatively charged in WT chicken IL-1β (FIG. 7B), whereas that region in the mutant chicken interleukin-1β protein having T117A or E118A mutation has a relatively greater area of positive charge than WT chicken IL-1β (FIGS. 7C and 7D, arrow indication). The result indicates that 3D change in the mutant chicken interleukin-1β protein can affect IL-1β signal transduction.

Example 7

3D Structural Model of Wild-Type IL-1β/IL-1 Receptor (IL-1R)/IL-1 Receptor Accessory Protein (IL-1 RAcP) Complex Triggering the chicken interleukin-1β signal transduction to nucleus and a cascade of immune response are needed WT IL-1β interacting with IL-1 receptor type I and IL-1 receptor accessory proton, but the 3D structural model of WT IL-1β/IL-1 receptor (IL-1R)/IL-1 receptor accessory protein (IL-1RAcP) complex is still unidentified, and the present invention simulates and analyzes structural model of the complex by the a platform for simulation and analysis of biochemical networks.

Figure 8A:
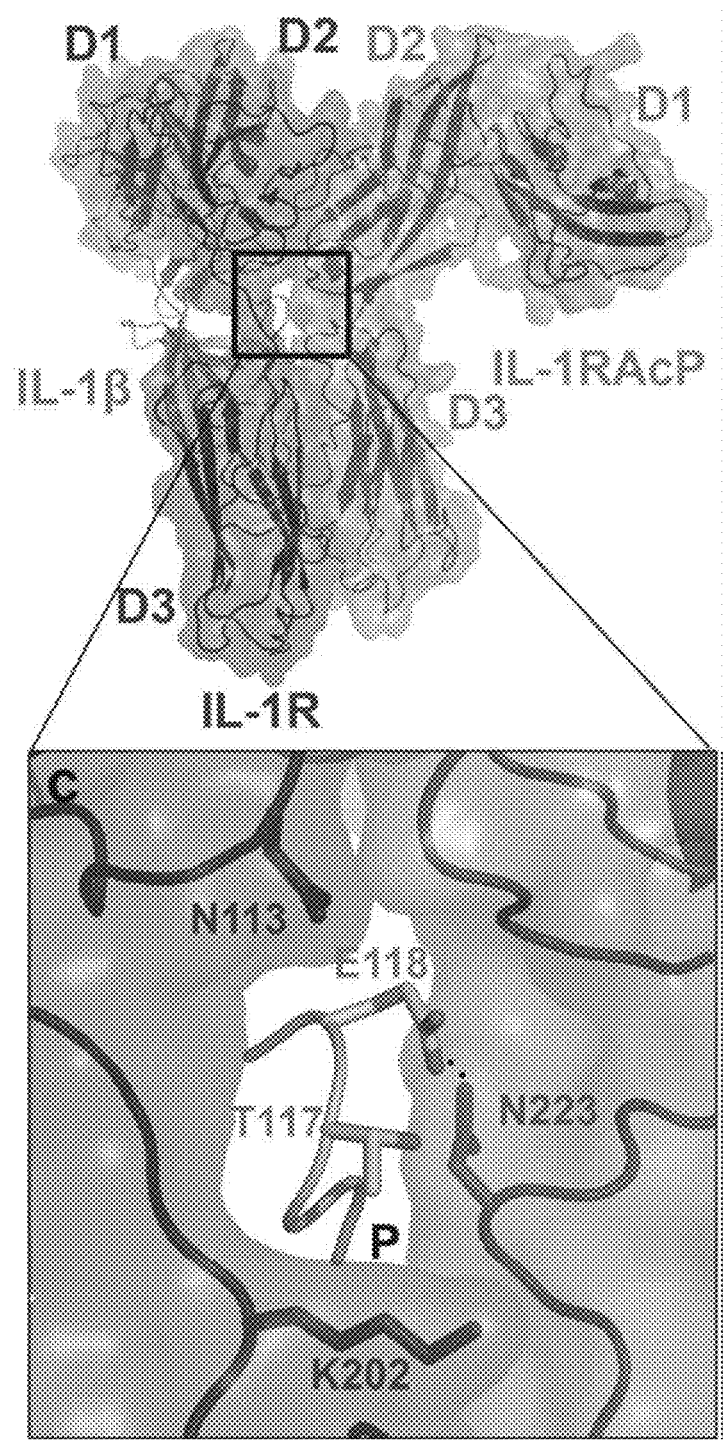
FIGS. 8A and 8B show 3D structural model of IL-1β/IL-1 receptor (IL-1R)/IL-1 receptor accessory protein (IL-1RAcP) complex. IL-1β is indicated wild-type chicken interleukin-1β; IL-1R is indicated IL-1β receptor; IL-RAcP is indicated IL-1β receptor accessory protein; and T117, E118, N113, N223 and K202 are indicated amino acid residues.
Figure 8B:
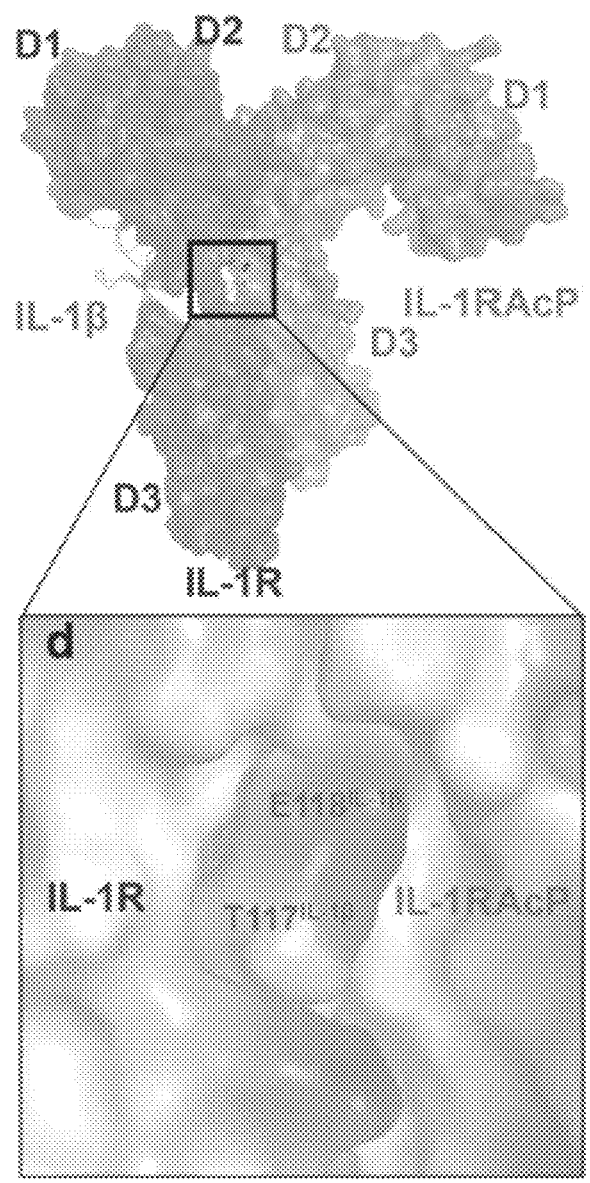

As shown in FIGS. 8A and 8B, the mutant chicken interleukin-1β protein by point mutation at WT chicken IL-1β residues T117 and E118 in a genetic engineering method is at IL-1 receptor (IL-1R)/IL-1 receptor accessory protein (IL-1RAcP) interface (FIGS. 8A and 8B, upper), which forms a pocket structure to allow a loop formed by WT chicken IL-1β residues T117 and E118 interacting with IL-1 receptor accessory protein (IL-1RAcP) and IL-1 receptor linker via hydrogen bonds and hydrophobic interactions (FIG. 8A, lower). The electrostatic potential surface involving residues T117 and E118 are more negatively charged than it surroundings, confined by IL-1 receptor (IL-1R)/IL-1 receptor accessory protein (IL-1RAcP) (FIG. 8B, lower), and the IL-1 receptor (IL-1R)/IL-1 receptor accessory protein (IL-1RAcP) interface is a positively charged surface to mutually attract with WT chicken IL-1β residue T117 and E118. If the polarity of amino acid side chains changes, such as the mutant chicken interleukin-1β protein of the present invention, the interface becomes too unstable to trigger a signal transduction and a cascade of immune response.

Example 8

The Mutant Chicken Interleukin-1β Protein Inhibits Viral Proliferation

To validate the mutant chicken interleukin-1β protein of the present invention as an antagonist against inducing high level expression of IL-1β, the present invention takes avian reovirus (ARV) for example. It is well-known that avian reovirus infection enters through the exposure of broken skin of the feet or digestive tract of the chickens to sequentially proliferate in the immune cells of joints and liver. The present invention respectively injects avian reovirus or avian reovirus mixing with the mutant chicken interleukin-1β protein hiving E118R mutation into the feet of specific pathogen free (SPF) chicken. The chicken is sacrificed after three days to cut joint and liver tissue into slices for immunohistochemical staining using specific monoclonal antibody σNS protein of avian reovirus.

Figure 9A:
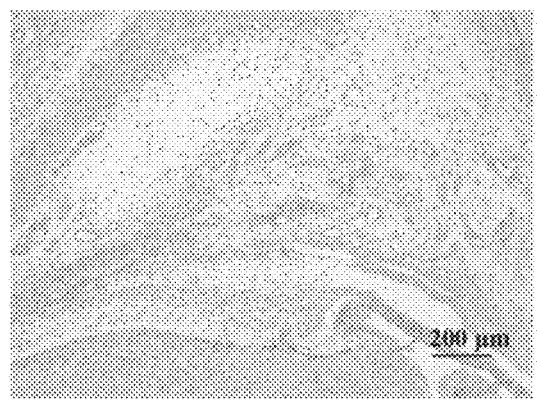
FIGS. 9A to 9C show immunohistochemistry staining of joint of specific pathogen free (SPF) chicken injected avian reovirus (ARV) or avian reovirus mixing with the mutant chicken interleukin-1β protein (ARV+E118R). PBS is indicated phosphate-buffered saline.
Figure 9B:
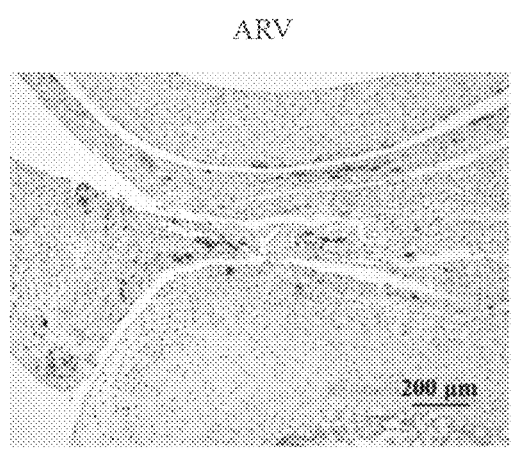
Figure 9C:
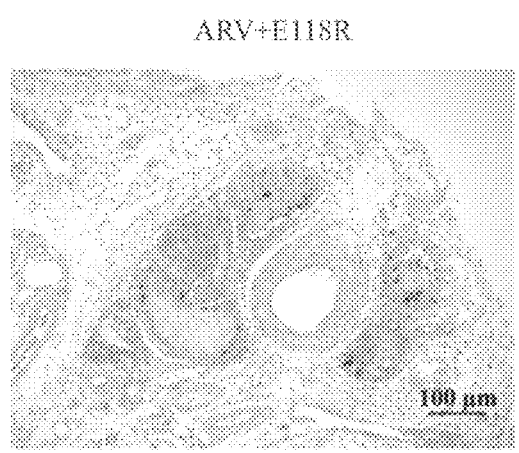
Figure 10A:
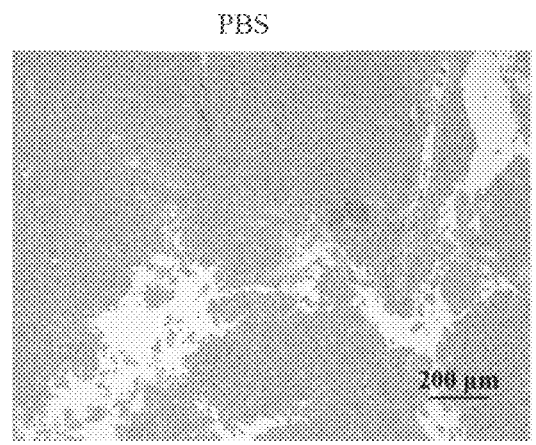
FIGS. 10A to 10C show immunohistochemistry staining of liver of specific pathogen free (SPF) chicken injected avian reovirus (ARV) or avian reovirus mixing with the mutant chicken interleukin-1β protein (ARV+E118R). PBS is indicated phosphate-buffered saline.
Figure 10B:
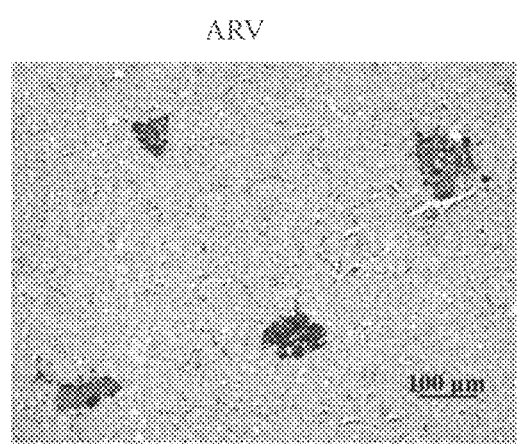
Figure 10C:
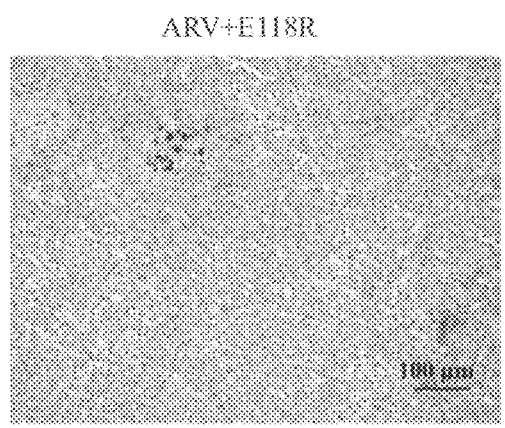

As shown in FIGS. 9A to 9C and FIGS. 10A to 10C, the SPF chicken only inoculated with ARV, tendon sheaths at synovial joints and subcutaneous tissue show strong positive signals of avian reovirus protein σNS (FIG. 9B), and a large area of liver cytoplasm shows strong positive signals of avian reovirus protein σNS (FIG. 10B). In contrast, the SPF chicken inoculated with ARV mixing with the mutant chicken interleukin-1β protein hiving E118R mutation, only granulomatous nodules around blood vessels in tendon sheaths at synovial joints show slight positive signals of avian reovirus protein σNS (FIG. 9C), and liver cells also show slight positive of avian reovirus protein σNS (FIG. 10C). Two tissues of the SPF chicken only inoculated phosphate-buffered saline (PBS) show no specific signal (FIGS. 9A and 10A). These animal experiment results have validated that the tissue from the chicken inoculated with ARV and the mutant chicken interleukin-1β protein shows less viral proliferation than that from the chicken only inoculated with ARV, therefore, the mutant chicken interleukin-1β protein can effectively inhibit viral proliferation in animal body.

To quantify the staining results of the animal experiments, the quantity level can be divided into 0 to 5 classes. Class 0 indicates no significant specific signal; class 1 indicates slight positive of avian reovirus protein σNS; class 5 indicates a large diffusion area of strong positive signals of avian reovirus protein σNS. As shown in Table 1, the SPF chicken only inoculated with ARV, tendon sheaths at synovial joints and liver tissue show strong positive signals of avian reovirus protein σNS (class 3). The SPF chicken inoculated with ARV mixing with the mutant chicken interleukin-1βprotein hiving E118R mutation, only tendon sheaths at synovial joints and liver tissue show slight positive signals of avian reovirus protein σNS (class 1).

TABLE 1

Quantifying immunohistochemical staining using specific monoclonal antibody σNS protein of avian reovirus

| | joint | liver |
|---|---|---|
| inoculating phosphate-buffered saline (PBS) | 0 | 0 |
| inoculating with avian reovirus (ARV) | 3 | 3 |
| inoculating with avian reovirus mixing with the mutant chicken interleukin-1β protein hiving E118R mutation (ARV + E118R) | 1 | 1 |

In summary, the present invention changes amino acid position 117 and 118 of WT chicken IL-1β to obtain the mutant chicken interleukin-1β protein having T117A, E118K or E118R mutation. The present invention obtains a soluble protein with high yield and high purity by high performance protein expression and purification platform. The present invention validates that the mutant chicken interleukin-1β protein has almost lost bioactivity by SPF chicken in vivo test, the secondary structure of WT chicken IL-1β and the mutant chicken interleukin-1β protein are similar by far-UV CD spectroscopy, and the binding affinity of WT chicken IL-1β and the mutant chicken interleukin-1β protein are also similar by surface plasmon resonance (SPR) study. Therefore, the mutant chicken interleukin-1β protein of the present invention does not change secondary structure, but losses the effect on IL-1β signal transduction that leads to loss bioactivity, and have similar receptor binding affinities compared with WT chicken IL-1β.

The present invention validates that the mutant chicken interleukin-1β protein antagonizes chicken IL-1β activity by competitive examination for cellular signaling. In addition, the present invention analyzes the mutant chicken interleukin-1β protein having T117A or E118K mutation by X-ray crystallographic structure determination platform to find that local secondary structure and charge are significant different from WT chicken IL-1β. The mutant chicken interleukin-1β protein by point mutation at WT chicken IL-1β residues 117 and 118 is at IL-1 receptor (IL-1R)/IL-1 receptor accessory protein (IL-1RAcP) interface to perform signal transduction; the changed interface becomes too unstable to trigger a signal transduction and a cascade of immune response.

Furthermore, the present invention validates that the mutant chicken interleukin-1β protein as a chicken interleukin-1β antagonist has the ability of inhibiting viral infection. Take avian reovirus (ARV) for example, the present invention respectively injects avian reovirus or avian reovirus mixing with the mutant chicken interleukin-1β protein hiving E118R mutation into the feet of specific pathogen free (SPF) chicken, and validates that the tissue from the chicken inoculated with ARV and the mutant chicken interleukin-1β protein having E118K mutation shows less viral proliferation than that from the chicken only inoculated with ARV by immunohistochemical staining using specific monoclonal antibody σNS protein of avian reovirus.

Comparable Example 1

Figure 11:
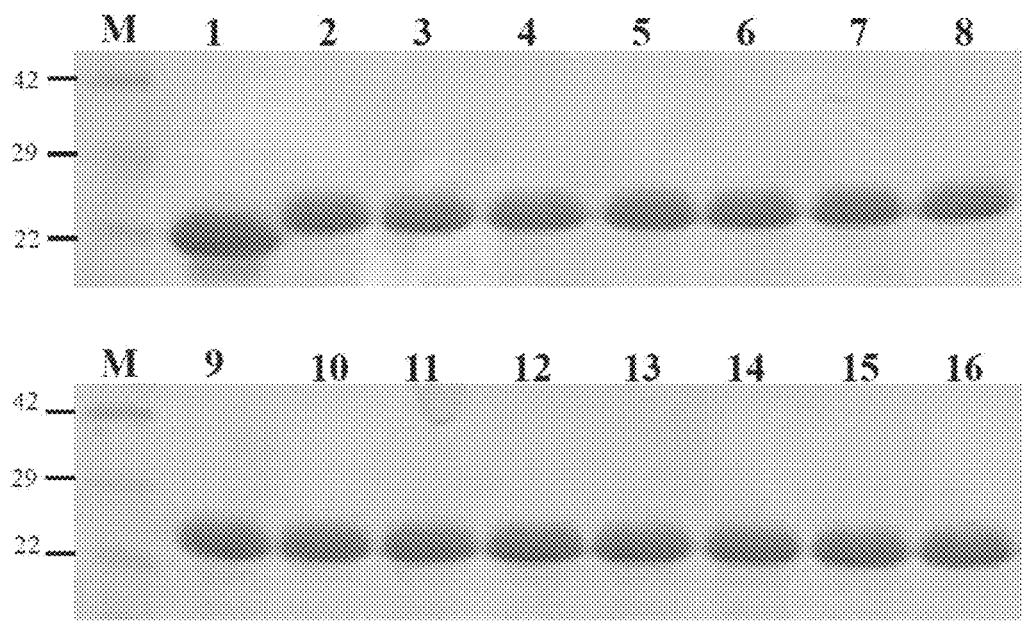
FIG. 11 is 12% sodium dodecyl sulfate polyacrylamide gel electrophoresis (SDS PAGE) of the mutant chicken interleukin-1β (IL-1β) protein having substitution mutation at other site or substituted with another amino acid after clone, mutant protein expression and purification. M is indicated marker; wild-type human IL-1β (lane 1); wild-type chicken IL-1β (lane 2); and the mutation chicken interleukin-1β protein having substitution mutation of T7A (lane 3), R8A (lane 4), N18A (lane 5), E25A (lane 6), H34A (lane 7), Q36A (lane 8), R52A (lane 9), R54A (lane 10), Q64A (lane 11), E118A (lane 13) and Q138A (lane 16), wherein the substitution mutation of E118A (lane 13) is indicated the mutant chicken interleukin-1β (IL-1β) protein substituted with another amino acid, others are indicated the mutant chicken interleukin-1β (IL-1β) protein having substitution mutation at other site; and the mutation chicken interleukin-1β protein having T117A lane 12), E118K (lane 14) and E118R (lane 15) mutation.

Bioactivity Assay of a Mutant Chicken Interleukin-1β Protein Having Other Substitution Mutations at Other Site or Substituted with Another Amino Acid To determine the mutant chicken interleukin-1β protein of the present invention having a mutation at key amino acid position, the present invention designs other mutation chicken interleukin-1β protein having T7A, R8A, N18A, E25A, H34A, Q36A, R52A, R54A, Q64A, E118A or Q138A mutation according to the procedure of EXAMPLE 1, and the mutation chicken interleukin-1β protein having E118A is indicated the mutation chicken interleukin-1β protein substituted with another amino acid at key amino acid position. The present invention obtains a soluble protein with high yield and high purity by high performance protein expression and purification platform, and validates that the molecular weight of those other mutation chicken interleukin-1β proteins is similar to that of WT chicken IL-1β. As show in FIG. 11, the molecular weight of WT human IL-1β (lane 1), WT chicken IL-1β (lane 2), and the mutation chicken interleukin-1β protein having T7A (lane 3), R8A (lane 4), N18A (lane 5), E25A (lane 6), H34A (lane 7), Q36A (lane 8), R52A (lane 9), R54A (lane 10), Q64A (lane 11), T117A (lane 12), E118A (lane 13), E118K (lane 14), E118R (lane 15) and Q138A (lane 16) mutation is 23.6 kDa by 12% sodium dodecyl sulfate polyacrylamide gel electrophoresis (SDS PAGE).

Figure 12:
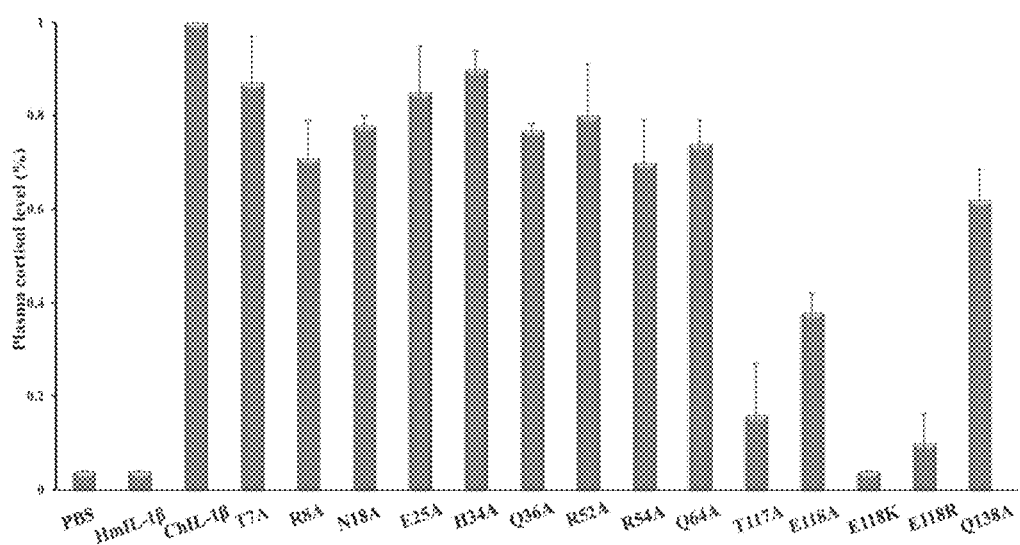
FIG. 12 shows that the plasma cortisol levels in chickens administrated the mutant chicken interleukin-1β protein having other substitution mutation. PBS is indicated phosphate-buffered saline; HmIL-1β wild-type human IL-1β; ChIL-1β is indicated wild-type chicken interleukin-1β; T7A, R8A, N18A, E25A, H34A, Q36A, R52A, R54A, Q64A, T117A, E118A, E118K, E118R and Q138A are respectively indicated the mutant chicken interleukin-1β protein having those substitution mutations.

Then, the present invention detects the plasma cortisol level to determine the in vivo activity of the mutant chicken interleukin-1β protein having substitution mutation at other site or substituted with another amino acid according to the procedure of EXAMPLE 2. The present invention respectively injects WT human IL-1β, WT chicken IL-1β, other mutation chicken interleukin-1β protein having T7A, R8A, N18A, E25A, H34A, Q36A, R52A, R54A, Q64A, E118A or Q138A mutation, and the mutation chicken interleukin-1β protein having T117A, E118K or E118R mutation into the wing vein of specific pathogen free (SPF) chicken, wherein the mutation chicken interleukin-1β protein having T7A, R8A, N18A, E25A, H34A, Q36A, R52A, R54A, Q64A or Q138A mutation is indicated a mutant chicken interleukin-1β protein having substitution mutation at other site, another mutation chicken interleukin-1β protein having E118A mutation substituted with another amino acid. As shown in FIG. 12, the plasma cortisol level resulted from responses to the mutant chicken interleukin-1β protein having T117A, E118K or E118R mutation relative to that of WT chicken interleukin-1β protein are 16%, 4% and 10%, respectively, which show a significantly decreased bioactivity; the plasma cortisol level resulted from responses to the mutant chicken interleukin-1β protein having E118A mutation relative to that of WT chicken interleukin-1β protein are 40%, which shows a decreased bioactivity; and the plasma cortisol level resulted from responses to the mutant chicken interleukin-1β protein having T7A, R8A, N18A, E25A, H34A, Q36A, R52A, R54A, Q64A or Q138A mutation relative to that of WT chicken interleukin-1β protein are 80% to 90%, respectively, which show a slightly decreased bioactivity. Therefore, these results validate that not all mutant chicken interleukin-1β protein having mutation has a decreased bioactivity. The mutant chicken interleukin-1β protein of the present invention has a mutation at key amino acid position (at amino acid position 117 and 118) to block in vivo chicken pro-inflammatory immune responses.

Accordingly, the present invention provides a novel chicken interleukin-1β antagonist to solve a difficult problem of poor animal vaccine effect. The cost of the mutant chicken interleukin-1β protein as a chicken interleukin-1β antagonist or an anti-viral medicine is 0.01 to 0.1 New Taiwan Dollars (TWD) for each chicken, it can be more lower cost resulted from mass production. Also, the mutant chicken interleukin-1β protein has good quality and stability, it can store at −20° C. to maintain activity for 6 months (not precipitation). Therefore, the mutant chicken interleukin-1β protein is more competitive in the international market. Moreover, all countries in the world including Taiwan have faced the problems of drug-resistance updates and new mutant recombinant virus, such as avian influenza virus, avian reovirus and Marek's disease virus. Therefore, the mutant chicken interleukin-1βprotein of the present invention can be used as a biological cytokine antagonist against virus to enhance vaccine effect and to protect livestock and poultry from disease threats. The present invention is a novel immunotherapy for antiviral and anti-inflammatory therapy.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A mutant chicken interieukin-1β protein that is derived from the chicken interleukin-1β comprising the amino acid sequence of SEQ ID NO:1, wherein the mutant comprises an amino acid substitution T117A, E118K, E118R or E118A in SEQ ID NO: 1.

2. The mutant chicken interleukin-1β protein of claim 1, which is a chicken interleukin-1β antagonist.

3. A method of treating a disease caused by avian virus infection, comprising administering to a subject in need thereof an effective amount of a medicament comprising the mutant chicken interieukin-1β protein of claim 1.

4. The method according to claim 3, wherein the avian virus infection is avian reovirus, avian influenza virus, Marek's disease virus or Newcastle disease virus infection.

5. The method according to claim 3, wherein the medicament is administered via an oral route or an intravenous injection.

6. The method according to claim 3, wherein the mutant chicken interleukin-1β protein inhibits proliferation of avian virus and avian inflammation response.

* * * * *

SEQUENCE LISTING

```
<160> NUMBER OF SEQ ID NOS: 18

<210> SEQ ID NO 1
<211> LENGTH: 162
<212> TYPE: PRT
<213> ORGANISM: Gallus gallus

<400> SEQUENCE: 1

Ala Pro Ala Phe Arg Tyr Thr Arg Ser Gln Ser Phe Asp Ile Phe Asp
1               5                   10                  15

Ile Asn Gln Lys Cys Phe Val Leu Glu Ser Pro Thr Gln Leu Val Ala
            20                  25                  30

Leu His Leu Gln Gly Pro Ser Ser Ser Gln Lys Val Arg Leu Asn Ile
        35                  40                  45

Ala Leu Tyr Arg Pro Arg Gly Pro Arg Gly Ser Ala Gly Thr Gly Gln
    50                  55                  60

Met Pro Val Ala Leu Gly Ile Lys Gly Tyr Lys Leu Tyr Met Ser Cys
65                  70                  75                  80
```

Val Met Ser Gly Thr Glu Pro Thr Leu Gln Leu Glu Glu Ala Asp Val
             85                  90                  95

Met Arg Asp Ile Asp Ser Val Glu Leu Thr Arg Phe Ile Phe Tyr Arg
            100                 105                 110

Leu Asp Ser Pro Thr Glu Gly Thr Thr Arg Phe Glu Ser Ala Ala Phe
            115                 120                 125

Pro Gly Trp Phe Ile Cys Thr Ser Leu Gln Pro Arg Gln Pro Val Gly
            130                 135                 140

Ile Thr Asn Gln Pro Asp Gln Val Asn Ile Ala Thr Tyr Lys Leu Ser
145                 150                 155                 160

Gly Arg

<210> SEQ ID NO 2
<211> LENGTH: 162
<212> TYPE: PRT
<213> ORGANISM: Gallus gallus

<400> SEQUENCE: 2

Ala Pro Ala Phe Arg Tyr Thr Arg Ser Gln Ser Phe Asp Ile Phe Asp
1               5                   10                  15

Ile Asn Gln Lys Cys Phe Val Leu Glu Ser Pro Thr Gln Leu Val Ala
            20                  25                  30

Leu His Leu Gln Gly Pro Ser Ser Gln Lys Val Arg Leu Asn Ile
            35                  40                  45

Ala Leu Tyr Arg Pro Arg Gly Pro Arg Gly Ser Ala Gly Thr Gly Gln
        50                  55                  60

Met Pro Val Ala Leu Gly Ile Lys Gly Tyr Lys Leu Tyr Met Ser Cys
65                  70                  75                  80

Val Met Ser Gly Thr Glu Pro Thr Leu Gln Leu Glu Glu Ala Asp Val
            85                  90                  95

Met Arg Asp Ile Asp Ser Val Glu Leu Thr Arg Phe Ile Phe Tyr Arg
            100                 105                 110

Leu Asp Ser Pro Ala Glu Gly Thr Thr Arg Phe Glu Ser Ala Ala Phe
            115                 120                 125

Pro Gly Trp Phe Ile Cys Thr Ser Leu Gln Pro Arg Gln Pro Val Gly
            130                 135                 140

Ile Thr Asn Gln Pro Asp Gln Val Asn Ile Ala Thr Tyr Lys Leu Ser
145                 150                 155                 160

Gly Arg

<210> SEQ ID NO 3
<211> LENGTH: 162
<212> TYPE: PRT
<213> ORGANISM: Gallus gallus

<400> SEQUENCE: 3

Ala Pro Ala Phe Arg Tyr Thr Arg Ser Gln Ser Phe Asp Ile Phe Asp
1               5                   10                  15

Ile Asn Gln Lys Cys Phe Val Leu Glu Ser Pro Thr Gln Leu Val Ala
            20                  25                  30

Leu His Leu Gln Gly Pro Ser Ser Gln Lys Val Arg Leu Asn Ile
            35                  40                  45

Ala Leu Tyr Arg Pro Arg Gly Pro Arg Gly Ser Ala Gly Thr Gly Gln
        50                  55                  60

Met Pro Val Ala Leu Gly Ile Lys Gly Tyr Lys Leu Tyr Met Ser Cys
65                  70                  75                  80

```
Val Met Ser Gly Thr Glu Pro Thr Leu Gln Leu Glu Ala Asp Val
            85                  90                  95

Met Arg Asp Ile Asp Ser Val Glu Leu Thr Arg Phe Ile Phe Tyr Arg
                100                 105                 110

Leu Asp Ser Pro Thr Lys Gly Thr Arg Phe Glu Ser Ala Ala Phe
            115                 120                 125

Pro Gly Trp Phe Ile Cys Thr Ser Leu Gln Pro Arg Gln Pro Val Gly
            130                 135                 140

Ile Thr Asn Gln Pro Asp Gln Val Asn Ile Ala Thr Tyr Lys Leu Ser
145                 150                 155                 160

Gly Arg

<210> SEQ ID NO 4
<211> LENGTH: 162
<212> TYPE: PRT
<213> ORGANISM: Gallus gallus

<400> SEQUENCE: 4

Ala Pro Ala Phe Arg Tyr Thr Arg Ser Gln Ser Phe Asp Ile Phe Asp
1               5                   10                  15

Ile Asn Gln Lys Cys Phe Val Leu Glu Ser Pro Thr Gln Leu Val Ala
                20                  25                  30

Leu His Leu Gln Gly Pro Ser Ser Gln Lys Val Arg Leu Asn Ile
            35                  40                  45

Ala Leu Tyr Arg Pro Arg Gly Pro Arg Gly Ser Ala Gly Thr Gly Gln
        50                  55                  60

Met Pro Val Ala Leu Gly Ile Lys Gly Tyr Lys Leu Tyr Met Ser Cys
65                  70                  75                  80

Val Met Ser Gly Thr Glu Pro Thr Leu Gln Leu Glu Ala Asp Val
            85                  90                  95

Met Arg Asp Ile Asp Ser Val Glu Leu Thr Arg Phe Ile Phe Tyr Arg
                100                 105                 110

Leu Asp Ser Pro Thr Arg Gly Thr Thr Arg Phe Glu Ser Ala Ala Phe
            115                 120                 125

Pro Gly Trp Phe Ile Cys Thr Ser Leu Gln Pro Arg Gln Pro Val Gly
            130                 135                 140

Ile Thr Asn Gln Pro Asp Gln Val Asn Ile Ala Thr Tyr Lys Leu Ser
145                 150                 155                 160

Gly Arg

<210> SEQ ID NO 5
<211> LENGTH: 26
<212> TYPE: DNA
<213> ORGANISM: Artificial Sequence
<220> FEATURE:
<223> OTHER INFORMATION: synthetic primer

<400> SEQUENCE: 5
cgcctggaca gcccggctga gggcac                                          26

<210> SEQ ID NO 6
<211> LENGTH: 25
<212> TYPE: DNA
<213> ORGANISM: Artificial Sequence
<220> FEATURE:
<223> OTHER INFORMATION: synthetic primer

<400> SEQUENCE: 6
```

```
cgtggtgccc tcagccgggc tgtcc                                          25

<210> SEQ ID NO 7
<211> LENGTH: 28
<212> TYPE: DNA
<213> ORGANISM: Artificial Sequence
<220> FEATURE:
<223> OTHER INFORMATION: synthetic primer

<400> SEQUENCE: 7
ctggacagcc cgactaaggg caccacgc                                       28

<210> SEQ ID NO 8
<211> LENGTH: 28
<212> TYPE: DNA
<213> ORGANISM: Artificial Sequence
<220> FEATURE:
<223> OTHER INFORMATION: synthetic primer

<400> SEQUENCE: 8
gaagcgcgtg gtgcccttag tcgggctg                                       28

<210> SEQ ID NO 9
<211> LENGTH: 28
<212> TYPE: DNA
<213> ORGANISM: Artificial Sequence
<220> FEATURE:
<223> OTHER INFORMATION: synthetic primer

<400> SEQUENCE: 9
ctggacagcc cgactcgggg caccacgc                                       28

<210> SEQ ID NO 10
<211> LENGTH: 28
<212> TYPE: DNA
<213> ORGANISM: Artificial Sequence
<220> FEATURE:
<223> OTHER INFORMATION: synthetic primer

<400> SEQUENCE: 10
gaagcgcgtg gtgccccgag tcgggctg                                       28

<210> SEQ ID NO 11
<211> LENGTH: 22
<212> TYPE: DNA
<213> ORGANISM: Artificial Sequence
<220> FEATURE:
<223> OTHER INFORMATION: synthetic primer

<400> SEQUENCE: 11
ggatccgccc gccttccgct ac                                             22

<210> SEQ ID NO 12
<211> LENGTH: 24
<212> TYPE: DNA
<213> ORGANISM: Artificial Sequence
<220> FEATURE:
<223> OTHER INFORMATION: synthetic primer

<400> SEQUENCE: 12
ctcgagtcag cgcccactta gctt                                           24

<210> SEQ ID NO 13
<211> LENGTH: 363
<212> TYPE: DNA
```

<213> ORGANISM: Artificial Sequence
<220> FEATURE:
<223> OTHER INFORMATION: synthetic sequence

<400> SEQUENCE: 13

| | | | | | | |
|---|---|---|---|---|---|---|
| gcgcccgcct | tccgctacac | ccgctcacag | tccttcgaca | tcttcgacat | caaccagaag | 60 |
| tgcttcgtgc | tggagtcacc | cacccagctg | gtggccctgc | acctccaggg | gccctcctcc | 120 |
| agccagaaag | tgaggctcaa | cattgcgctg | taccggcccc | gaggcccacg | ggcagcgct | 180 |
| ggaactgggc | agatgccagt | ggcactgggc | atcaagggct | acaagctcta | catgtcgtgt | 240 |
| gtgatgagcg | gcaccgagcc | cacactgcag | ctggaggaag | ccgacgtcat | gcgggacatc | 300 |
| gacagcgtcg | agctgacccg | cttcatcttc | taccgcctgg | acagcccggc | tgagggcacc | 360 |
| acg | | | | | | 363 |

<210> SEQ ID NO 14
<211> LENGTH: 156
<212> TYPE: DNA
<213> ORGANISM: Artificial Sequence
<220> FEATURE:
<223> OTHER INFORMATION: synthetic sequence

<400> SEQUENCE: 14

| | | | | | | |
|---|---|---|---|---|---|---|
| tcagcgccca | cttagcttgt | aggtggcgat | gttgacctgg | tcgggttggt | tggtgatgcc | 60 |
| cacgggctgc | cggggctgca | gggaggtgca | gatgaaccac | ccggggaagg | cggccgactc | 120 |
| gaagcgcgtg | gtgccctcag | ccgggctgtc | caggcg | | | 156 |

<210> SEQ ID NO 15
<211> LENGTH: 369
<212> TYPE: DNA
<213> ORGANISM: Artificial Sequence
<220> FEATURE:
<223> OTHER INFORMATION: synthetic sequence

<400> SEQUENCE: 15

| | | | | | | |
|---|---|---|---|---|---|---|
| gcgcccgcct | tccgctacac | ccgctcacag | tccttcgaca | tcttcgacat | caaccagaag | 60 |
| tgcttcgtgc | tggagtcacc | cacccagctg | gtggccctgc | acctccaggg | gccctcctcc | 120 |
| agccagaaag | tgaggctcaa | cattgcgctg | taccggcccc | gaggcccacg | ggcagcgct | 180 |
| ggaactgggc | agatgccagt | ggcactgggc | atcaagggct | acaagctcta | catgtcgtgt | 240 |
| gtgatgagcg | gcaccgagcc | cacactgcag | ctggaggaag | ccgacgtcat | gcgggacatc | 300 |
| gacagcgtcg | agctgacccg | cttcatcttc | taccgcctgg | acagcccgac | taagggcacc | 360 |
| acgcgcttc | | | | | | 369 |

<210> SEQ ID NO 16
<211> LENGTH: 153
<212> TYPE: DNA
<213> ORGANISM: Artificial Sequence
<220> FEATURE:
<223> OTHER INFORMATION: synthetic sequence

<400> SEQUENCE: 16

| | | | | | | |
|---|---|---|---|---|---|---|
| tcagcgccca | cttagcttgt | aggtggcgat | gttgacctgg | tcgggttggt | tggtgatgcc | 60 |
| cacgggctgc | cggggctgca | gggaggtgca | gatgaaccac | ccggggaagg | cggccgactc | 120 |
| gaagcgcgtg | gtgcccttag | tcgggctgtc | cag | | | 153 |

<210> SEQ ID NO 17
<211> LENGTH: 369

```
<212> TYPE: DNA
<213> ORGANISM: Artificial Sequence
<220> FEATURE:
<223> OTHER INFORMATION: synthetic sequence

<400> SEQUENCE: 17
gcgcccgcct tccgctacac ccgctcacag tccttcgaca tcttcgacat caaccagaag      60
tgcttcgtgc tggagtcacc cacccagctg gtggccctgc acctccaggg gccctcctcc     120
agccagaaag tgaggctcaa cattgcgctg taccggcccc gaggcccacg gggcagcgct     180
ggaactgggc agatgccagt ggcactgggc atcaagggct acaagctcta catgtcgtgt     240
gtgatgagcg gcaccgagcc cacactgcag ctggaggaag ccgacgtcat gcgggacatc     300
gacagcgtcg agctgacccg cttcatcttc taccgcctgg acagcccgac tcggggcacc     360
acgcgcttc                                                              369

<210> SEQ ID NO 18
<211> LENGTH: 153
<212> TYPE: DNA
<213> ORGANISM: Artificial Sequence
<220> FEATURE:
<223> OTHER INFORMATION: synthetic sequence

<400> SEQUENCE: 18
tcagcgccca cttagcttgt aggtggcgat gttgacctgg tcgggttggt tggtgatgcc      60
cacgggctgc cggggctgca gggaggtgca gatgaaccac ccggggaagg cggccgactc     120
gaagcgcgtg gtgccccgag tcgggctgtc cag                                   153
```